US006605105B1

(12) United States Patent
Cuschieri et al.

(10) Patent No.: US 6,605,105 B1
(45) Date of Patent: Aug. 12, 2003

(54) INSTRUMENT OR FORCEPS FOR MEDICAL AND PARTICULARLY ENDOSCOPIC APPLICATIONS

(75) Inventors: Alfred Cuschieri, St. Andrews (GB); Timothy Graham Frank, Wormit Newport-On-Tay (GB)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/545,322

(22) Filed: Apr. 7, 2000

Related U.S. Application Data

(63) Continuation of application No. PCT/DE98/03017, filed on Oct. 14, 1998.

(30) Foreign Application Priority Data

Oct. 14, 1997 (DE) .......................................... 197 45 157

(51) Int. Cl.[7] .............................................. A61B 17/28
(52) U.S. Cl. ..................................................... 606/208
(58) Field of Search ................................ 606/198, 191, 606/205–210; 604/106–109

(56) References Cited

U.S. PATENT DOCUMENTS

| 5,235,966 A | * | 8/1993 | Jay ............................. 600/198 |
| 5,353,784 A | * | 10/1994 | Nady-Mohamed .......... 600/205 |
| 5,549,636 A | | 8/1996 | Li |
| 5,630,831 A | | 5/1997 | Lahr |
| 5,695,515 A | * | 12/1997 | Orejola ........................ 606/191 |

FOREIGN PATENT DOCUMENTS

| DE | 44 31 561 A1 | 3/1996 |
| EP | 0 640 319 A1 | 3/1995 |

* cited by examiner

Primary Examiner—Kevin T. Truong
(74) Attorney, Agent, or Firm—St. Onge Steward Johnston & Reens LLC

(57) ABSTRACT

What is described here is an instrument for medical and particularly endoscopic applications, comprising
  a proximally disposed operating unit,
  a distally disposed multi-part functional element having individual parts which are jointly and additionally independently movable, such as a multi-part forceps jaw, and
  an elongate connecting part which is disposed between the operating unit and said forceps jaw.

The invention is characterized by the provisions that said operating unit is so configured that it can be grasped around by one hand, and that said operating unit comprises at least two pivotable and/or tiltable elements which are a component of the surface of said operating unit and which, when moving, control each one part of said multi-part functional element.

31 Claims, 4 Drawing Sheets

INSTRUMENT OR FORCEPS FOR MEDICAL AND PARTICULARLY ENDOSCOPIC APPLICATIONS

This application is a continuation of PCT/DE98/03017 filed Oct. 14, 1998.

FIELD OF THE INVENTION

The present invention relates to an instrument for medical applications, and particularly to an instrument for endoscopic applications which includes a multi-part functional element (for example, end effectors or forceps jaws) and an operating unit for the operation of the functional element for effecting a surgical operation.

PRIOR ART

Endoscopic instruments such as forceps or pincers have become known wherein the jaws of the forceps is adapted to perform not only simple opening or closing movements, respectively, as this is the case with the forceps known from the document WO 94/20034. For an explanation of all details not described here in more details explicit reference is made, by the way, to that prior art document.

For instance, the most different instruments are known which present two or more functional elements on their distal end, which can be pivoted or displaced along the longitudinal axis of the instrument and which are adapted to perform mutually independent movements and, if necessary, movements linked up with each other.

Furthermore, instruments or forceps have become known wherein the jaws of the forceps present a multi-part configuration. In an exemplary manner reference should be made in this context to the German Patent DE 694 03 583 T2.

Moreover, manipulators with multi-part function elements for holding or spreading tissue etc. have become known from the Japanese Patent 06311984 A, the European Patent EP 0 688 538 A1 or the U.S. Pat. No. 5,549,636.

The functional elements in the known instruments are operated, as a rule, by scissors or pushing handles or by elements into which the operator can introduce his or her fingers. These elements translate the movement of the fingers into a movement of the distal functional elements. In this respect additional reference is made to the U.S. Pat. No. 5,630,831 or the European Patent EP 0 613 762 A1.

Additionally, handles with operating elements for several functions have become known.

The operating units so far used in prior art are, however, unsatisfactory from an ergonomic point of view, especially when more than one distal functional element must be operated. Furthermore, the known operating units are not intuitive. The movement which the operator is required to perform on the operating element frequently hardly resembles the movement to be performed by the corresponding functional element in terms of direction and kind of movement.

Under certain conditions this may result in serious errors in operation of these instruments in the course of a surgical operation.

BRIEF DESCRIPTION OF THE INVENTION

The present invention is based on the problem of simplifying the operation of instruments, particularly those including a plurality of functional elements, in such a way that an intuitive, simple and safe operation will be possible.

One inventive solution to this problem is defined in Patent claim 1. Improvements of the invention are the subject matters of the dependent claims.

In accordance with the present invention, the operating unit is so configured that it can be grasped by one hand, and comprises at least two circumferential elements (e.g., at least two pivotable and/or tiltable elements) which are components of the surface of the operating unit and which, by their movement, control each one part of the multi-part functional element. It is particularly preferable that the operating unit is so configured that it serves also as handle for holding the instrument.

The operator can thus hold the instrument with one hand only and control, at the same time, the distally disposed functional elements by moving individual fingers or finger joints, respectively. Grasping is furthermore facilitated it the elements are configured, at least approximately, as segments of a rotational body such as a cylinder or a sphere.

In any case, the inventive configuration presents the particular advantage that the operator can grasp the operating unit by his or her complete hand, with the rear part bearing against the thenar region and is fixed thereby. One pressure by the thenar against the rear end may serve to move the functional elements as a single unit, i. e. jointly.

Another ergonomic improvement is achieved when gripping depressions are provided for the fingers. This provision supports the intuitive operation in particular.

From an ergonomic point of view it is particularly expedient to provide two elements coupled to each other, which are adapted for being tilted in different directions for moving the individual parts of the functional elements. The elements are preferably connected to via linkages to sliding elements which, in their turn, are connected to rods moving the functional elements on the distal end.

In an alternative embodiment of the invention four segments may be provided whereof two respective ones are coupled to each other. The mutually coupled segments are arranged symmetrically relative to a plane including the longitudinal axis of the connecting element.

Due to the mutually coupled segments, which are formed symmetrically relative to a plane including the longitudinal axis of the connecting element, a symmetrical operation free of a tilting momentum is achieved for the functional elements provided on the distal end.

Both designs may be used to operate one or several functional elements.

It is possible to articulate the segments provided on the proximal side to a stationary part of the instrument and to couple it via a pushing bar to a sliding element connected to the second connecting rod. The segments disposed on the distal side are then articulated on the segments provided on the proximal side and coupled via a pushing rod to a sliding element, which is connected to the first connecting rod.

It is moreover advantageous to bias the operating elements into a position in which the functional elements take a defined position. In the event of functional elements configured as jaws of forceps it is then preferable that the defined position is that position in which the forceps jaws are open.

Independently of the particular configuration of the instrument or the forceps, respectively, it is preferable that the operating elements are biased into a position in which the functional or jaw elements, respectively, take a defined position also under the aspect set out below, because in such a case the operator working with the instrument can always change the instrument into an initial or basic position when the operating unit is released. This "initial position" may be that position, for instance, in which the two parts of each jaw element are open.

It is moreover expedient to provide locking elements by means of which the parts of each functional or jaw element, respectively, can be locked in a defined position. With these provisions the operator can lock the instrument in a position which is advantageous or ergonomically expedient for the respective surgical or examination operation.

It is furthermore advantageous to make provisions for a rotation of the connecting element and hence of the functional or jaw element disposed on its distal end about its longitudinal axis, such as this is known, for example, from the document WO 94/20034. It is possible to provide a wheel on the connecting element for rotation of the distal end, which wheel when operated rotates the connecting element. In this design various catch positions may be provided.

The inventive solutions apply to both rigid and flexible instruments.

If the multi-part functional elements are multi-part forceps they may have, of course, also the function of scissors or a cutting function, in addition to a mere forceps function. To this end all the known forms of jaws may be employed; even a roughening of the surface may be provided in order to prevent a lateral deflection of the object.

Claims 22–31 define a multi-part forceps device as an example of a multi-part functional element, wherein each mobile jaw element consists of two parts whereof one part, i.e. the part on the proximal side, is articulated on the connecting element whilst the other part, i.e. the part on the distal side, is articulated on the proximal part directly or via a lever mechanism. The parts of the two jaw elements on the proximal side and the parts of the two jaw elements on the distal side are movable independently of each other. With this provision it is possible that the operator is able to pivot the two jaw elements not only as a single unit but can bend them also in a manner similar to the joint of a finger. With this design it is possible, for instance, to grasp a bundle or tract of tissue by "grasping around it" rather than only on one side in a "squeezing" manner. Hence sensitive, and even fairly large objects can be grasped carefully and reliably and yet the forceps jaws may be approached to a very small diameter.

It should be emphasised here, however, expressis verbis, that the most different functional elements, which need not at all be restricted to forceps or scissors but can be designed in any form whatsoever—as is known from prior art—may, of course, be controlled with the operating unit configured in accordance with the present invention.

BRIEF DESCRIPTION OF THE DRAWING

The present invention will now be described, without any limitation of the general inventive idea, by exemplary embodiment with reference to the drawing which is referred to explicitly in all other respects as far as the disclosure of all inventive details is concerned which are not explained in a more detailed form in the text. In the drawing.

DESCRIPTION OF EMBODIMENTS

Figure 1:
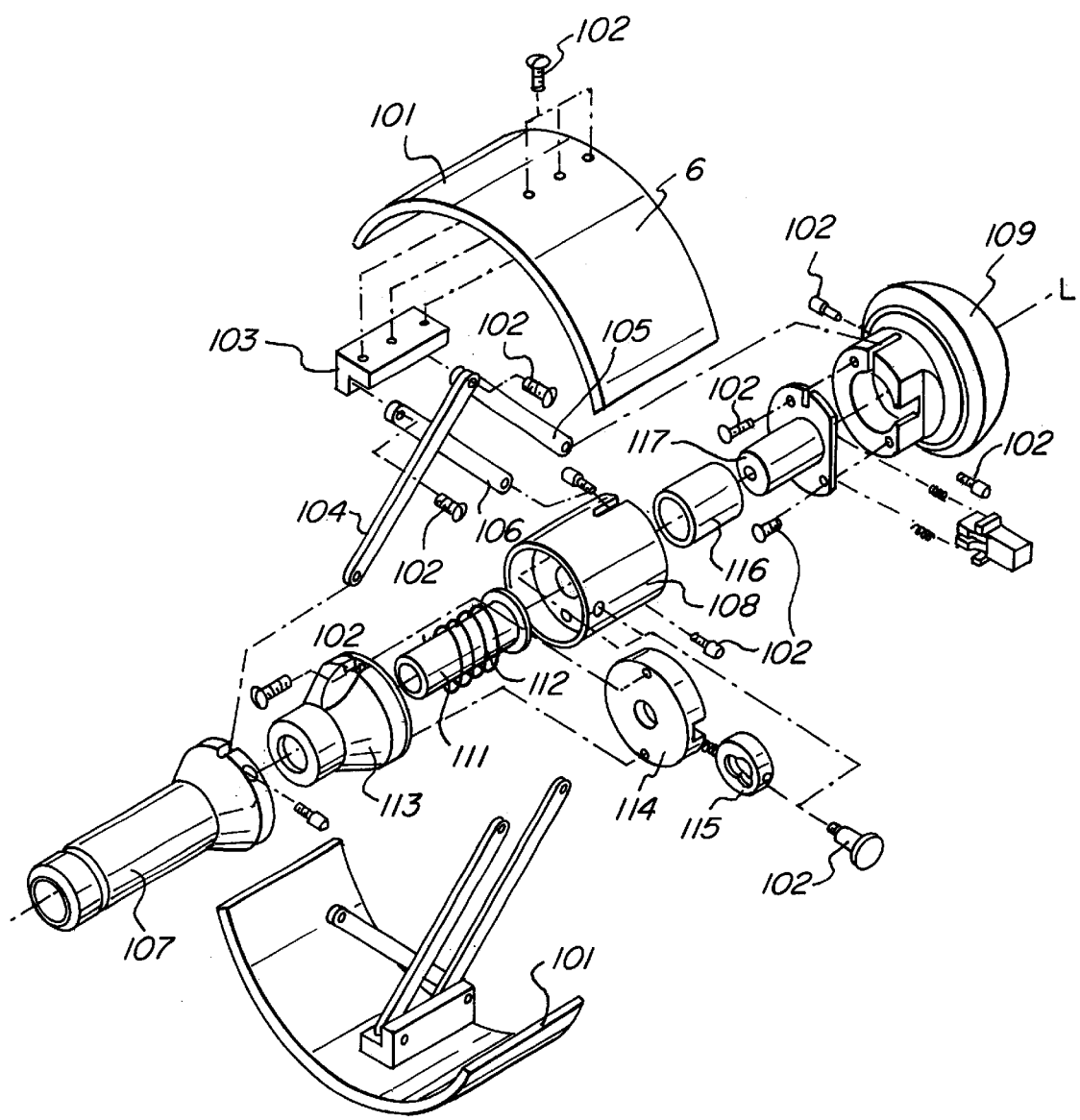
FIG. 1 illustrates a first embodiment of an operating unit configured in accordance with the invention, in an exploded view.

FIG. 1 is an exploded view of the operating unit of a first embodiment of an inventive instrument. The distal portion, which may be designed in any form whatsoever and which is shown in FIG. 4 merely as an example, is not illustrated.

The operating unit comprises two elements, i.e., two semi-annular members 101 which are manipulatable (e.g., pivotable or tiltable) in a forward and rearward direction along the longitudinal axis L of the instrument and which are components of the surface of the operating unit. A fastening block 103 is mounted by means of screws 102 on each element 101, on which block a linkage is articulated, again by means of screws 102, which consists of a plurality of link elements, e.g., three rods 104, 105 and 106. Ergonomically adapted gripping depressions G, which are not illustrated in details, may be provided on the elements 101.

The rod 104 is articulated by its rear or proximal end (in the direction of the longitudinal axis L) of the fastening block 103, together with the rod 105, whereas the rod 106 is articulated on the front end. The respectively other ends of the rods 104, 105 and 106 are articulated on a sliding element 107, a socket 108 or at the rear end portion 109 of the operating unit.

A second transmitting element (not illustrated in this Figure and shown merely in FIG. 4), which has a tubular configuration, is fastened on the distal end of the sliding element 107 and transmits the sliding element to a distal functional element, which is not shown either in FIG. 1. A first transmitting element is coaxially disposed in the tube.

A pin 111, on which a spring 112 is guided, is fixedly connected to the sliding element 107. The pin 111 is guided in a guide 113 which is fastened via screws 102 and intermediate elements 114 and 115 on the socket 108. Moreover, the other end of the rod 105 is articulated on the socket 108, as has been set out in the foregoing. A sleeve 116 is adhesively fastened on the proximal end of the socket 108, which is guided on a pin 117 which is screwed on the proximal end part 109. For further details, reference is made to the drawing.

The two transmitting elements can be individually shifted in a forward direction and hence the functional elements can be operated individually by tilting the elements 101 in a forward or rearward direction. By pressing the proximal end part 109 in a forward direction it is possible move the functional element as a single unit.

Figure 2:
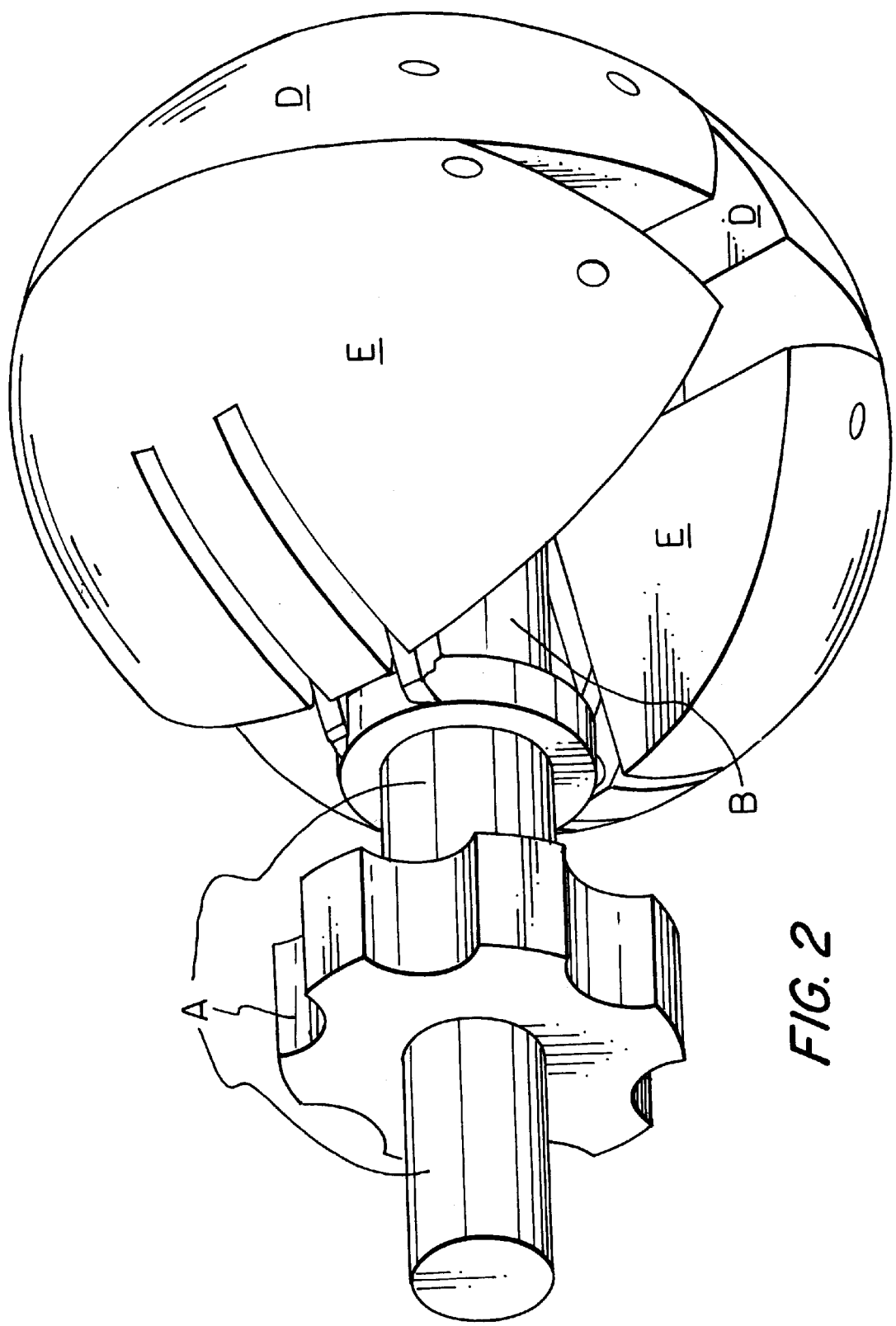
FIG. 2 is a perspective view of a second embodiment of an operating unit designed in correspondence with the present invention.

FIG. 2 is a perspective unit of the operating unit of a second embodiment, which can be used instead of the operating unit shown in FIG. 1. Moreover, this operating unit—in a simplified embodiment—is also suitable for instruments in which merely a distal functional element is actuated by shifting a rod in the connecting element.

The mode of operation of the second embodiment will now be explained with reference to the sectional views shown in FIGS. 3a–3c.

In this embodiment, too, the operating unit is the handle at the same time. The operating unit is taken by the operator's hand in such a way that it is enclosed by the hand and bears against the thenar by its proximal end.

In the illustrated second embodiment the operating unit has the shape of a sphere which is subdivided into four segments D, D, E and E whereof respectively two, i. e. the segments D and D or E and E are coupled to each other. The mutually coupled segments are provided in symmetry relative to a plane containing the longitudinal axis L of the connecting element.

The segments D arranged on the proximal side are articulated in a stationary part C of the instrument and coupled, via a pushing rod H, to a sliding element A which is connected to the second transmitting rod. The segments E, which are disposed on the distal side, are articulated on segments D arranged on the proximal side and coupled, via a pushing rod G, to a sliding element B which is connected to the first transmitting rod. The element A and B slide on the element C while the element E rotates on D and D rotates on C.

Figure 3A:
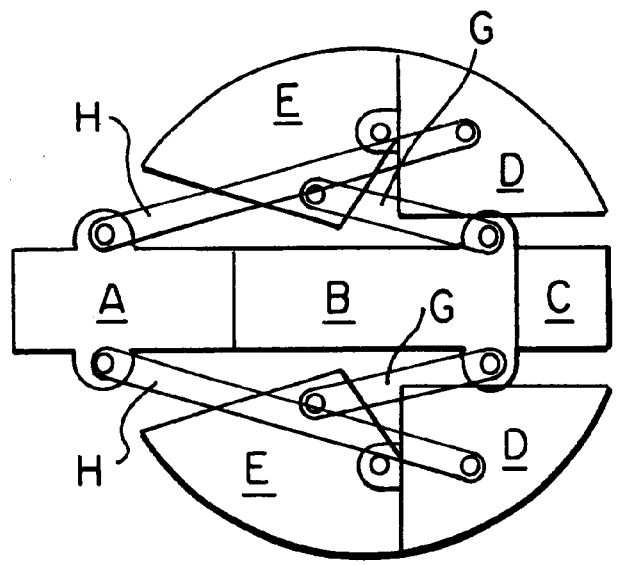
FIGS. 3a–3c are sectional views taken through the operating unit for an explanation of the mode of operation.
Figure 3B:
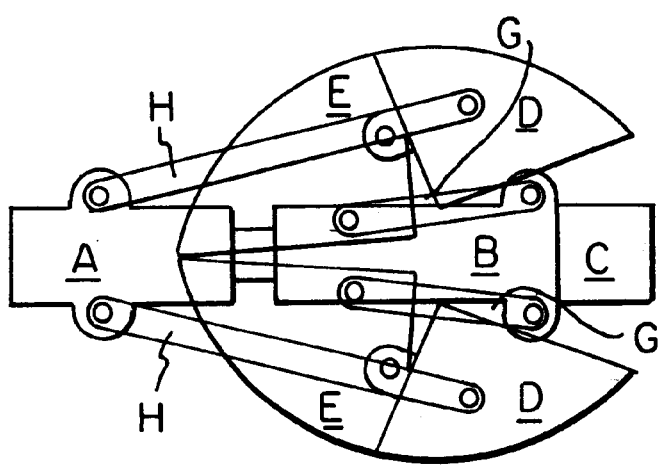
Figure 3C:
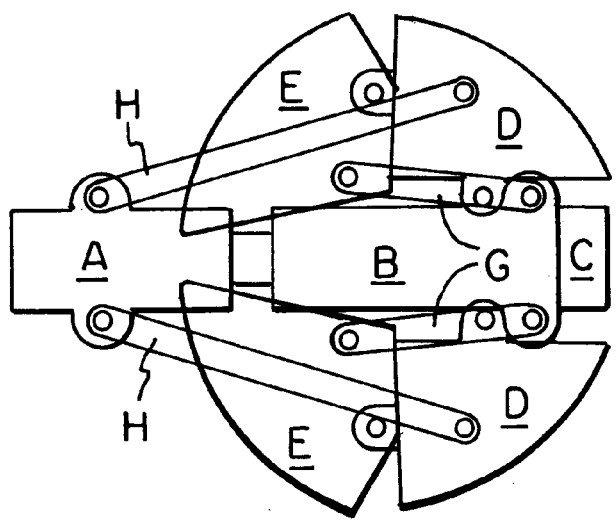

FIGS. 3a to 3c show different positions of the operating element, with equal parts being provided with equal reference numerals.

FIG. 3b illustrates the position in which merely the segments D are operative. As a result the sliding element A, which is connected to the second transmitting rod, is displaced so that (for instance in the case of a two-part forceps instrument) the parts on the distal side of the jaw element are actuated.

FIG. 3c shows the position in which the forward segments E are operated. As a result, the sliding element B, which is connected to the first transmitting rod, is displaced so that in the foregoing example the parts on the proximal side of the jaw element are actuated.

Figure 4A:
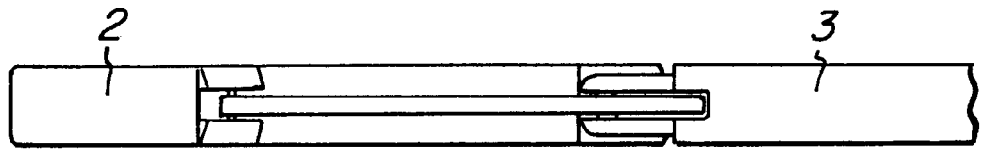
FIGS. 4a–4c show a perspective illustration of an example of the interior structure of the second embodiment.
Figure 4B:
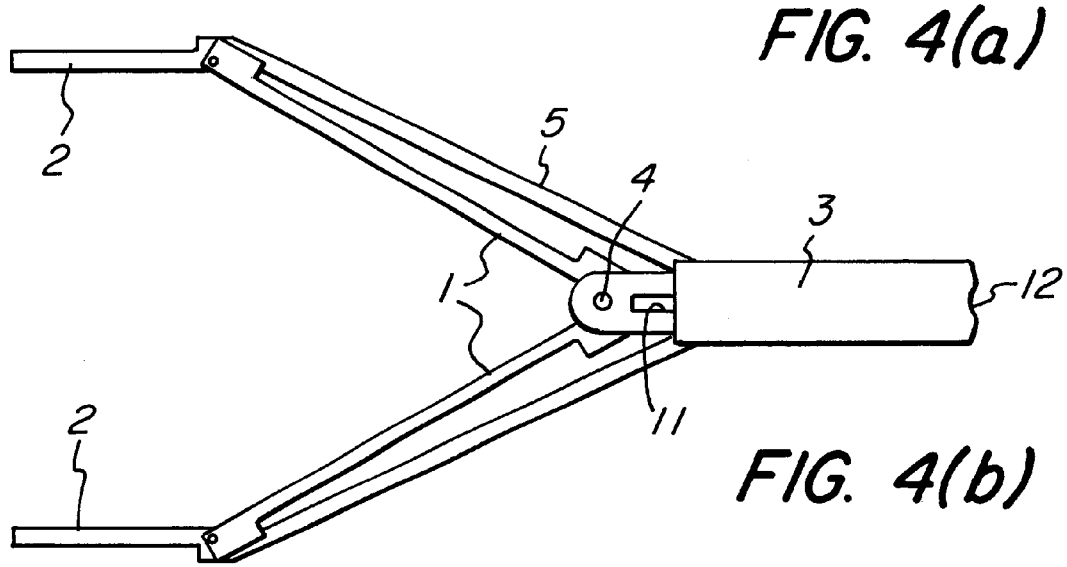
Figure 4C:
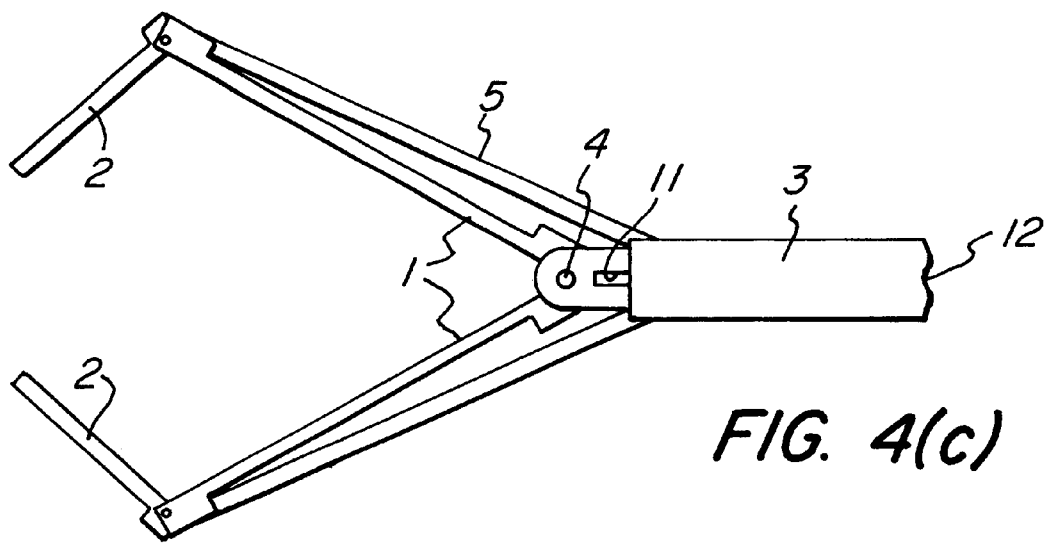

FIGS. 4a–4c illustrate a forceps jaw assembly as an example of a conceivable functional element in various positions, i.e. in the closed position (FIG. 4a), the completely open position (FIG. 4b), and in a position in which, for instance, a tract of tissue can be enclosed (FIG. 4c).

The illustrated forceps jaw comprises two jaw elements in a well-known manner. Each jaw element consists of two parts, i.e. a part 1 on the proximal side, which is articulated on a connecting part 3 for connection to a proximal forceps part, and a part 2 (e.g. jaw) on the distal side, which is articulated on the part 1 on the proximal side of the jaw element.

Two transmitting rods 11 and 12 are provided in the connecting part 1, whereof the rod 12 has a tubular design and surrounds the rod 11. A displacement of the rod 11 privots an element 4 which thereby moving opens or closes the parts 1, respectively. A displacement of the rod 12 causes, via a linkage 5, the parts 2 to move relative to the parts 1 so that the parts 2 of the forceps jaw assembly, which are disposed on the distal side, can be moved independently of the parts 1 disposed on the proximal side. This is illustrated in FIGS. 4a to 4c.

The present invention has been described in the foregoing without any restriction of the general inventive idea, and particularly the application of optional distal functional elements.

What is claimed is:

1. Instrument for surgical applications, comprising:
 a multi-part functional element for effecting a surgical or diagnostic operation on a patient;
 a shaft assembly disposed proximally to said functional element and extending along a longitudinal axis, said shaft assembly including a first and a second transmitting elements, each of the transmitting elements being movable, respectively, between a first position and a second position for the operation of said functional element; and
 an operating unit disposed adjacent a proximal side of said shaft assembly and defining an outer surface configured such that said operating unit can be grasped around by a hand with the thenar holding against the proximal end of the shaft assembly, said operating unit including at least two circumferential elements operatively coupled to said shaft assembly for selectively actuating movement of the transmitting elements, respectively, between the first position and the second position, thereby enabling a surgical or diagnostic operation of said functional element on a patient.

2. The instrument of claim 1, wherein the at least two circumferential elements of the operating unit include two semi-annular members, each semi-annular member being coupled to the shaft assembly through at least one link element disposed there-between.

3. The instrument of claim 2, wherein the shaft assembly further includes at least one sliding element movable along the longitudinal axis, and said each semi-annular member is coupled to the at least one sliding member of the shaft assembly for the operation of the functional element.

4. The instrument of claim 2, wherein each semi-annular member is coupled to the shaft assembly by three link elements.

5. The instrument of claim 2, wherein the two semi-annular members are manipulatable in different directions with respect to the shaft assembly for the operation of the functional element.

6. The instrument of claim 5, wherein the two semi-annular members are tiltable or pivotable in different directions with respect to the shaft assembly for the operation of the functional element.

7. The instrument of claim 1, wherein the operating unit is configured and dimensioned such that it can be served as a handle for holding the instrument.

8. The instrument of claim 7, wherein the operating unit is configured and dimensioned such that the at least two circumferential elements of the operating unit can be manipulated by one hand for the operation of the functional element.

9. The instrument of claim 8, wherein the circumferential elements of the operating unit include gripping depressions for facilitating grasping of the instrument by the fingers.

10. The instrument of claim 1, wherein the at least two circumferential elements of said operating unit include four segments, the segments being coupled to each other and connected to said shaft assembly by a plurality of link elements disposed therein.

11. The instrument of claim 10, wherein the segments are tiltable or pivotable in different directions with respect to the shaft assembly for the operation of the functional element.

12. The instrument of claim 11, wherein the segments coupled to each other are arranged in symmetry relative to the longitudinal axis of the shaft assembly.

13. The instrument of claim 12, wherein the segments as a whole define a generally sphere-like shape.

14. The instrument of claim 13, wherein the shaft assembly further includes a first and a second sliding elements, each being moveable along a stationary shaft portion of the shaft assembly, and the first sliding element being located proximally to the second sliding element.

15. The instrument of claim 14, wherein the two segments located on the proximal side thereof are articulated on the stationary shaft portion of the shaft assembly and are coupled to the second sliding element through the respective link elements, and the other two remaining segments are articulated on the two proximal segments and are coupled to the first sliding element.

16. The instrument of claim 1, wherein the operating unit is biased into a position in which the functional element have a defined position.

17. The instrument of claim 16, wherein the defined position of the functional element is an open position configured to receive an object therein.

18. The instrument of claim 16, wherein the operating unit includes a locking element adapted to lock the operating unit in the defined position.

19. The instrument of claim 1, wherein the shaft assembly includes a connecting element rotatable about the longitudinal axis of the shaft assembly, the connecting element being operable in association with at least one of the transmitting elements for the operation of the functional element.

20. The instrument of claim 19, wherein the connecting element includes a wheel for the rotation thereof.

21. The instrument of claim 1, wherein the functional element is a forceps jaw assembly.

22. The instrument of claim 21, wherein the forceps jaw assembly includes a pair of jaw elements, each jaw element including a proximal member coupled to one of the transmitting elements and a distal jaw coupled to the other of the transmitting elements.

23. The instrument of claim 22, wherein the respective proximal member is coupled to the first transmitting element and the respective distal jaw is coupled to the second transmitting element.

24. The instrument of claim 23, wherein the first transmitting element is coaxially arranged in the second transmitting element having a tubular design.

25. The instrument of claim 22, wherein the pair of jaw elements are movable as a single unit by pressing the proximal end of the shaft assembly.

26. The instrument of claim 22, wherein the distal jaw of each jaw element is movable independently of the proximal member of the jaw element by manipulation of the operating unit.

27. The instrument of claim 26, wherein the proximal member and the distal jaw of the jaws elements are pivotable.

28. The instrument of claim 27, wherein the jaws elements has a gripping or clamping function.

29. The instrument of claim 27, wherein the jaws elements has a cutting or removing function.

30. The instrument of claim 27, wherein the jaws elements has a cutting or removing function.

31. The instrument of claim 27, wherein the jaws elements are so configured as to permit spreading of openings thereby.

* * * * *